Nov. 3, 1959 R. W. CUMMING Plant Pat. 1,876
CHRYSANTHEMUM PLANTS
Filed July 3, 1957
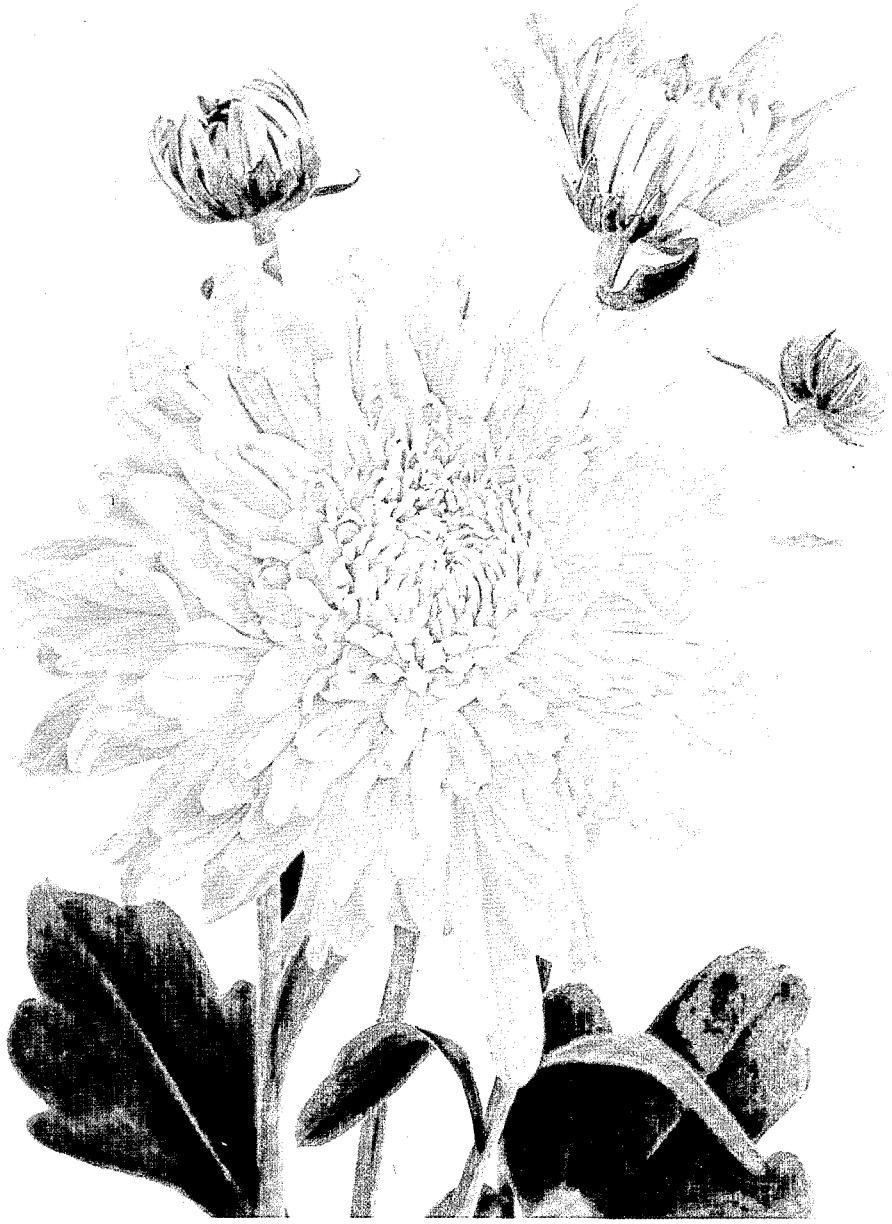
INVENTOR
Roderick W. Cumming
By Orville M Kile
Plant Patent Agent United States Patent Office Plant Pat. 1,876
Patented Nov. 3, 1959

1,876

CHRYSANTHEMUM PLANTS

Roderick W. Cumming, Bristol, Conn., assignor to Bristol Nurseries, Inc., Bristol, Conn.

Application July 3, 1957, Serial No. 669,905

1 Claim. (Cl. 47—60)

My present invention relates to a new and distinct variety or chrysanthemum plant of the "decorative" class which was originated by me at our Bristol nurseries by crossing the variety Aristocrat (unpatented) with a seedling of the variety Violet (unpatented).

The primary objective of this cross was to produce a new chrysanthemum variety combining the large, well-formed blossom of Aristocrat with the relative earliness of bloom of the variety Violet. This objective was achieved, along with the following characteristics displayed by the new variety:

(1) The thickly floriferous blooming habit on compact, stalwart plants.

(2) The very healthy, yellow-green foliage which remains on the plant all the way to the ground.

(3) The stiff, upright stems.

(4) The good productivity, large size, decorative form, and long season of the flowers.

(5) The distinctive color tonality of the flowers of Rhodamine Purple, with Grenadine Pink near the centers.

The foregoing characteristics and distinctions definitely differentiate my new variety from its parents, as well as from all other varieties of its class of which I am aware.

Asexual reproduction of the new variety by top cuttings, performed by me at Bristol, Connecticut through several succeeding propagations, shows that these characteristics and distinctions are firmly established.

The accompanying illustration shows typical specimens of the buds and flowers of my new chrysanthemum variety in various stages of development, together with some of the vegetative growth—all in as nearly true colors as it is reasonably possible to show in a color illustration of this character.

Following is a detailed description of my new variety of chrysanthemum, with color terminology in accordance with Ridgway's Color Standards and Nomenclature, except that where color plate numbers are not given the ordinary dictionary meaning of the term is intended.

Parentage: Aristocrat × seedling of Violet.

Observations: Made from specimens grown in a field at Bristol, Connecticut, mid-morning, in early October.

Cold resistance: Winter-hardy in central Connecticut if protected by winter covering. Flower quite frost-resistant.

Blooming period: In the Bristol area blooming starts about September 25 and continues until extreme freezing weather.

Blooming habit: Prolific producer of large, decorative-type flowers.

Growth habit: Free and strong, producing compact, stalwart plants which attain a height of from 24 to 32 inches.

*The plant*

Stems: Stiff and upright.

Foliage:

*Size.*—Large, measurement of a typical mature leaf being approximately 2½ by 3½ inches on a well-grown plant.

*Quantity.*—Normal, remaining all the way to the ground.

*Shape.*—Lobes rounded and somewhat scalloped in early stages. Mature leaves much more deeply cut and lobe more pointed.

*Color.*—Upper side, approximately Dark Dull Yellow Green (Pl. XXXII). Reverse side, Deep Dull Yellow Green (Pl. XXXII).

*The flower*

Bud:

*Size.*—About 1 inch wide as it begins to show color.

*Form.*—At first rounded and flattened in form, becoming an informal, cactus shape as it opens.

*Opening.*—Opens slowly.

*Bracts.*—Heavy and uneven in length.

*Color.*—When sepals first divide, Spinel Red (Pl. XXVI); when petals begin to unfurl, Spinel Pink (Pl. XXVI); when one-fourth to one-half open, inside of petal, Rosolane Purple (Pl. XXVI) and reverse of petal Spinel Pink (Pl. XXVI).

*Peduncle.*—Strength—very strong. Length—often as long as 12 inches. Color—Leaf Green (Pl. XLI).

Bloom:

*Size.*—Uniformly large, averaging from 3½ to 4 inches in diameter; occasionally larger.

*Stem.*—Strong, stiff, upright.

*Petalage (or number of florets).*—Very double.

*Color.*—Center of flower approximately Grenadine Pink (Pl. II); outer petals approximately Rhodamine Purple (Pl. XXII) with tips of petals Rhodamine Purple highlighted with Mallow Purple (Pl. XXII); inside of petals, Rosolane Purple (Pl. XXVI); reverse of petals, Mallow Purple (Pl. XXII).

*Petals.*—Texture—firm. Form—outer petals long and rather flat; inner petals somewhat spoon-shaped and short. Size—outer petals measure at least 2½ inches in the larger blooms. Fragrance—lightly characteristic of chrysanthemum odor.

Having thus disclosed my invention, I claim:

The new and distinct variety of chrysanthemum plant of the decorative type, substantially as herein shown and described, characterized particularly as to novelty by a combination of its compact habit of plant growth; its very healthy, yellow-green foliage which remains on the plant all the way to the ground; its strong upright stems; its excellent flower productivity, beginning early and continuing throughout a long season; and its very large, decorative-type flowers with general color tonality of Rhodamine Purple with Grenadine Pink centers.

No references cited.